United States Patent [19]

Hattori

[11] 4,422,457
[45] Dec. 27, 1983

[54] SAFETY DEVICE FOR MEDICAL TREATMENT SYSTEM

[75] Inventor: Shinichiro Hattori, Tokyo, Japan

[73] Assignee: Olympus Optical Co., Ltd., Tokyo, Japan

[21] Appl. No.: 279,327

[22] Filed: Jul. 1, 1981

[30] Foreign Application Priority Data

Jul. 14, 1980 [JP] Japan .................................. 55-95872

[51] Int. Cl.³ .......................... A61B 17/36; A61B 1/06
[52] U.S. Cl. ..................................... 128/303.1; 128/6;
128/303.15
[58] Field of Search ........................ 128/303 R, 6, 4, 5,
128/7, 8, 303.1, 303.15, 395–398; 340/573

[56] References Cited

U.S. PATENT DOCUMENTS 3,273,458 9/1966 Kohler .
3,906,953 9/1975 Wallace .
4,209,225 6/1980 Kumiomi et al. .................... 350/518

FOREIGN PATENT DOCUMENTS 2065710 2/1975 Fed. Rep. of Germany .......... 128/6

Primary Examiner—Michael H. Thaler
Attorney, Agent, or Firm—Frishauf, Holtz, Goodman & Woodward

[57] ABSTRACT

A medical treatment system provided with a safety device which prevents laser beams from being unnecessarily projected on a normal coeliac tissue around an affected coeliac region requiring medical treatment from a laser knife apparatus. When the operator approaches an eyepiece and is at a prescribed distance therefrom, then the safety device removes a mirror from a path of laser beams, enabling laser beams to be brought into a laser knife probe when a foot switch is closed. An infrared ray detector is provided in the eyepiece. When the operator approaches the eyepiece and is at the prescribed distance therefrom, an output signal from the infrared ray detector will be at a prescribed level. As a result, a solenoid controller is actuated to energize a solenoid. The mirror is removed from a path of the laser beams by the energized solenoid. Unless the operator approaches the eyepiece, the mirror remains in the path of laser beams, thereby preventing laser beams from being brought into the laser knife probe.

11 Claims, 7 Drawing Figures

SAFETY DEVICE FOR MEDICAL TREATMENT SYSTEM

BACKGROUND OF THE INVENTION

This invention relates to a medical treatment system, and more particularly to a safety device for an implement for carrying out medical treatment during observation, for example, a high frequency electric knife probe or laser knife probe attached to an endoscope apparatus.

A known medical treatment system attached to an endoscope apparatus includes a high frequency electric knife probe and a laser knife probe. Such probe is inserted into a coeliac cavity of a patient from a control section of an endoscope, a and medical operation is carried out, while the coeliac cavity is observed by the endoscope. In addition to an endoscope apparatus, a microsurgery device is put to practical use which applies a high frequency knife while observation is made by an operation type microscope.

If erroneously actuated, these medical treatment devices rise to serious danger to a patient, and consequently never fail to be provided with a safety device. Various proposals have already been advanced with respect to the safety device as set forth in, for example, Japanese utility model disclosures 50-58,590, 55-12,942 and 55-37,610. However, these proposals relate to the physical damage or displacement of a medical treatment device. To date, no proposal has been made with respect to protecting against an erroneous operation of a medical treatment device. Therefore, it has often happened that the erroneous operation of the above-mentioned medical treatment device by the user led to the undesirable excision or damage by burning of a normal coeliac tissue of a patient around an affected spot, and further the user himself suffered an injury by being exposed to, for example, laser beams.

It is accordingly the object of this invention to provide a medical treatment system provided with a safety device which causes the system to be actuated only when a medical treatment is carried out.

SUMMARY OF THE INVENTION

To attain the above-mentioned object, this invention provides a medical treatment system which comprises:

a medical optical apparatus which is provided with an eyepiece section to observe a coeliac region to be medically treated;

means for applying a medical treatment to a desired spot in a coeliac region requiring medical treatment;

switch means for energizing said medical treatment means;

detection means for detecting the approach of the operator of the medical treatment system to the eyepiece section, and generating an output signal which is a function of the distance between the operator and the eyepiece section;

judgment means for determining the operator's approach to the eyepiece section within a prescribed extent from an output signal of the detection means and issuing a medical treatment-enabling signal; and medical treatment-disabling means which normally maintains the medical treatment means in a disabled state, and enables said medical treatment means only when receiving a medical treatment-enabling signal from the judgment means.

This invention can be more fully understood from the following detailed description when taken in conjunction with the accompanying drawings.

DETAILED DESCRIPTION

Figure 1:
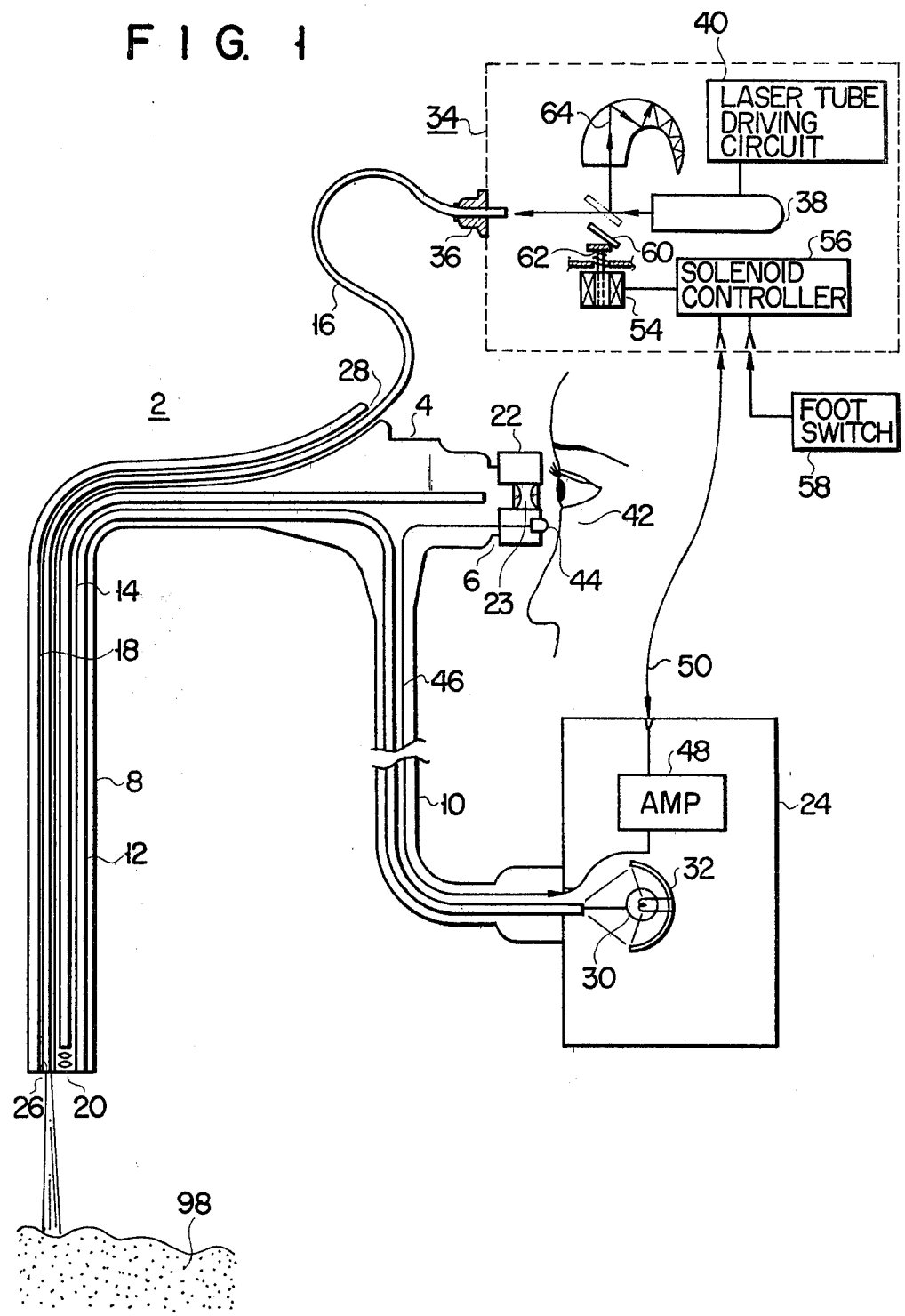
FIG. 1 is a block diagram of an endoscope system according to a first embodiment of this invention which is provided with a laser knife apparatus.

FIG. 1 shows a safety device for a laser knife apparatus attached to an endoscope system according to a first embodiment of this invention.

As is well known, an endoscope 2 comprises a control section 4, eyepiece section 6, insertion section 8 and universal cord 10. A light guide 12 and image guide 14 extends through the insertion section 8. A channel 18 for insertion of a laser knife probe 16 also extends through the insertion section 8. One end of the image guide 14 is positioned close to an object lens 20 fixed to a distal end of the insertion section 8. The image guide 14 extends through the control section 4, and the other end thereof is disposed near an eyepiece lens 23 fixed to an eyepiece frame 22 of the eyepiece section 6. One end of the light guide 12 is set at the distal end of the insertion section 8. The light guide 12 extends through the control section 4 and flexible tube 10. The other end of the light guide 12 is set in a light source device 24 connected to the flexible tube 10. The channel 18 communicates with an opening formed at the distal end of the flexible tube 10 and an opening 28 of the control section 4. A lamp 30 and light-focussing mirror 32 are so arranged in the light source device 24 as to cause a light to be brought to one end of the light guide 12. The light source device 24 comprises a light source circuit (not shown) including, for example, the lamp 30.

A laser knife apparatus 34 is fitted with a laser device connector 36 for attachment of the laser knife probe 16. A laser tube 38 is so set to cause laser beams to be brought to the light-receiving plane of the laser knife probe 16 fitted to said connector 36. The laser knife apparatus 34 further comprises a drive circuit 40 which is connected to the laser tube 38 for its actuation.

A medical treatment system embodying this invention is provided with an infrared beam detector 44 which detects the approach of the operator 42 to the eyepiece frame 22 and his separation therefrom. A signal line 46 of the infrared beam detector 44 extends through the eyepiece section 6, control section 4 and flexible tube 10 to the interior of the light source device 24 and is connected to a buffer amplifier 48 in said light source device 24. An output signal line 50 of the buffer amplifier 48 is connected to a solenoid control circuit 56 for controlling the operation of a solenoid 54 provided in the laser knife apparatus 34. This laser knife apparatus 34 is connected to a laser irradiation switch of, for example, the foot type. The solenoid 54 is fitted with a mirror 60. When the solenoid 54 is deenergized, the mirror 60 is set in a laser beam path extending from the laser tube 38 to the end face of the laser knife probe 16 in a state biased by a spring 62. An attenuator 64 for attenuating laser beams is disposed in a path of laser beams reflected by the mirror 60.

Figure 2:
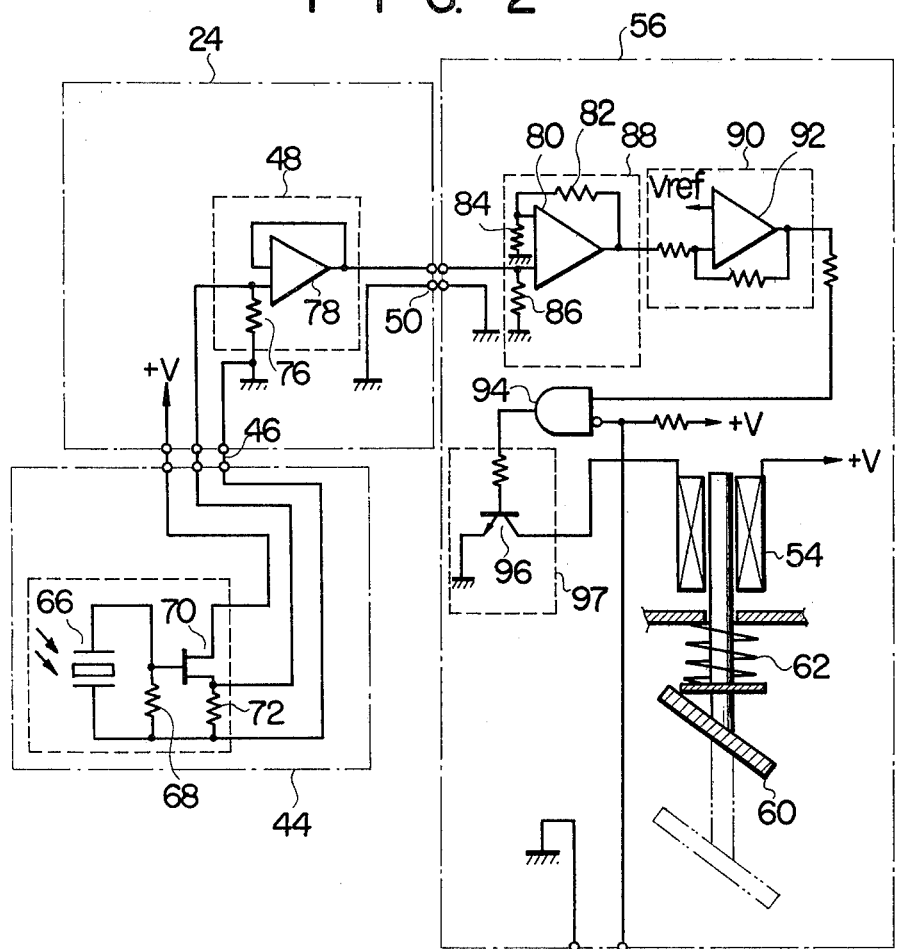
FIG. 2 shows the detailed arrangement of the electrical circuit of FIG. 1.

A circuit including the infrared beam detector 44, buffer amplifier 48 and solenoid control circuit 56 is arranged as shown in FIG. 2. In the infrared beam detector 44, a resistor 68 is connected in parallel to an infrared detection element 68. The resistor 68 is connected to a gate of an FET 70 and the drain of the FET. The drain of the FET unit 70 is connected to a power source +V by means of the signal line 46. The resistor 72 is connected in parallel to a resistor 76 of the buffer amplifier 48 by means of the signal line 46. The resistor 76 is connected between the noninverting terminal of an operation amplifier 78 constituting an voltage-follower and the ground. The output terminal of the operation amplifier 78 is connected through the signal line 50 to an amplifier 88 of the solenoid control circuit 56. Said amplifier 88 comprises an operation amplifier 80 and resistors 82, 84, 86. The ground of the buffer amplifier 48 and the ground of the control circuit 56 are jointly grounded through the signal line 50. The output terminal of the amplifier 88 is connected to the noninverting terminal of an operation amplifier 92 constituting a Schmitt circuit 90 having a hysteresis characteristic. The inverting terminal of said operation amplifier 92 is connected to a reference voltage source $V_{ref}$. The output terminal of the Schmitt circuit 90 is connected to one of the input terminals of the gate circuit 94. The other input terminal of the gate circuit 94 is connected to the power source +V and grounded through the foot switch 58. The output terminal of the gate circuit 94 is connected to the base of a transistor 96 constituting a solenoid drive circuit 97. The collector of the transistor 96 is connected to the power source +V through the solenoid 54. The emitter of the transistor 96 is grounded.

The laser knife apparatus 34 attached to the endoscope system arranged as described above carries out medical treatment in the undermentioned manner. First, the insertion section 8 of the endoscope 2 is taken into a coeliac cavity of a patient. The laser knife probe 16 is pushed through the opening 28 of the control section 4. The laser knife probe 16 is let to pass through the channel 18 to have the leading end of said laser knife probe 16 positioned at the distal end of the insertion section 8. When the operator 42 approaches a point separated from the eyepiece section 6 at a smaller distance than a prescribed distance, then the laser knife apparatus 34 is made ready to emit laser beams. When the operator 42 approaches the eyepiece section 6, then infrared beams reflected from the operator 42 enter the infrared beams-detecting element 66 of the infrared beam detector 44. A signal denoting the quantity of infrared beams detected by the infrared beam detector 44 is amplified by the buffer amplifier 48 and the amplifier 88 of the solenoid control circuit 56 and supplied to the Schmitt circuit 90 of the solenoid control circuit 56. The supplied signal increases in level, as a distance between the operator 42 and eyepiece section 6 is reduced. When this distance approaches a level falling within a prescribed range, then the level of the supplied signal reaches a threshold level defined by the reference voltage $V_{ref}$. When a signal denoting the detection of an infrared beam has a higher level than the threshold level, then the output terminal of the Schmitt circuit 90 sends forth a high level signal, that is, a signal enabling the emission of laser beams. The high level signal is supplied to one of the input terminals of the gate circuit 94. As a result, the solenoid control circuit 56 is brought to a state enabling the emission of laser beams.

When the operator 42 observes a coeliac region 98 to be medically treated through the eyepiece section 6, and the aim of the laser knife probe 16 is defined, then a laser beam irradiation switch 58 is closed, causing laser beams to be irradiated on the aforementioned coeliac region 98.

When the laser beam irradiation switch 58 is closed, then the other input terminal of the gate circuit 94 has its level changed from high to low. As a result, an output signal from the gate circuit 94 has its level changed from low to high. Accordingly, the transistor 96 of the solenoid coil drive circuit 97 is rendered conducting, thereby electric power being supplied from the power source +V to the solenoid coil 54. Therefore, the mirror 60 is attracted against the urging force of the spring 62. When the mirror 60 is removed from the path of laser beams emitted from the laser tube 38, then the laser beams are irradiated on the coeliac region 98 requiring medical treatment through the laser knife probe 16.

When the laser irradiation switch 58 is opened, the other input terminal of the gate circuit 94 has its level changed from low to high. As a result, an output signal from said gate circuit 94 has its level changed from high to low, thereby deenergizing the solenoid drive circuit 97. At this time the mirror 60 is positioned in the path of laser beams emitted from the laser tube 38 by the urging force of the spring 62. Consequently, laser beams issued from the laser tube 38 are not brought into the laser knife probe 16, but are reflected from the mirror 60 to the attenuator 64 to be attenuated.

When the operator 42 is separated from the eyepiece section 6 at a longer distance than the prescribed distance, then a quantity of infrared red beams entering the infrared beam detector 44 decreases. As a result, a signal supplied to the Schmitt circuit 90 has its level decreased from the threshold level, causing the level of an output signal from the Schmitt circuit 90 to be reduced from high to low. Even if, therefore, the laser beam switch 58 is closed by mistake, causing the other input terminal of the gate circuit 94 to fall to the low level, the mirror 60 is still held in the path of laser beams emitted from the laser tube 38, thereby preventing laser beams from being carried into the laser knife probe 16.

Figure 3:
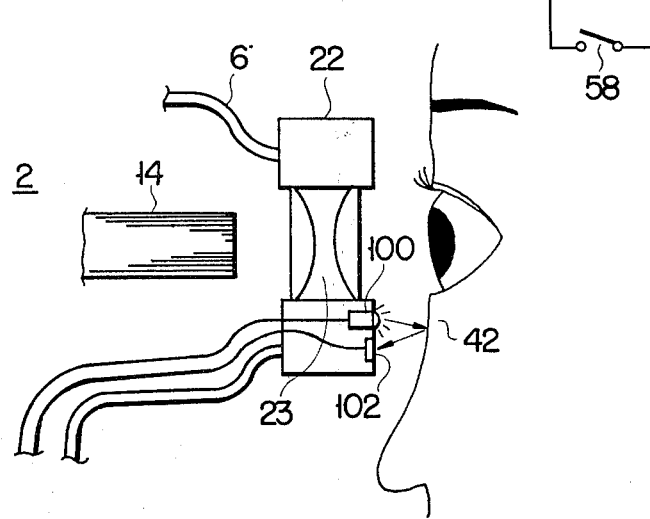
FIG. 3 schematically illustrates the eyepiece section of an endoscope system according to a second embodiment of the invention.

The infrared-detecting element 66 of the safety device of a medical treatment system embodying this invention may be replaced by an assembly (FIG. 3) of a light-emitting element 100 and light-receiving element 102. In other words, this alternative arrangement (see FIG. 4) is effected by the steps of:

fitting the eyepiece frame 22 with a light-emitting element 100, for example, a light-emitting diode and a light-receiving element 102, for example, a phototransistor in order to cause a light issued from the light-emitting element 100 to be reflected from the operator 42 and thereafter brought into the light-receiving element 102;

connecting the light-emitting element 100 to a D.C. source 24 provided in the light source device 24 through a resistor 105; and connecting the light-receiving element 102 to a current-voltage converter 107 provided in the light source device 103.

The current-voltage converter 107 is connected to the amplifier 88 of the solenoid control circuit 56 as in the embodiment of FIG. 2. Description is omitted of the solenoid control circuit 56 of FIG. 4 which is of the same type as that of FIG. 2.

Figure 4:
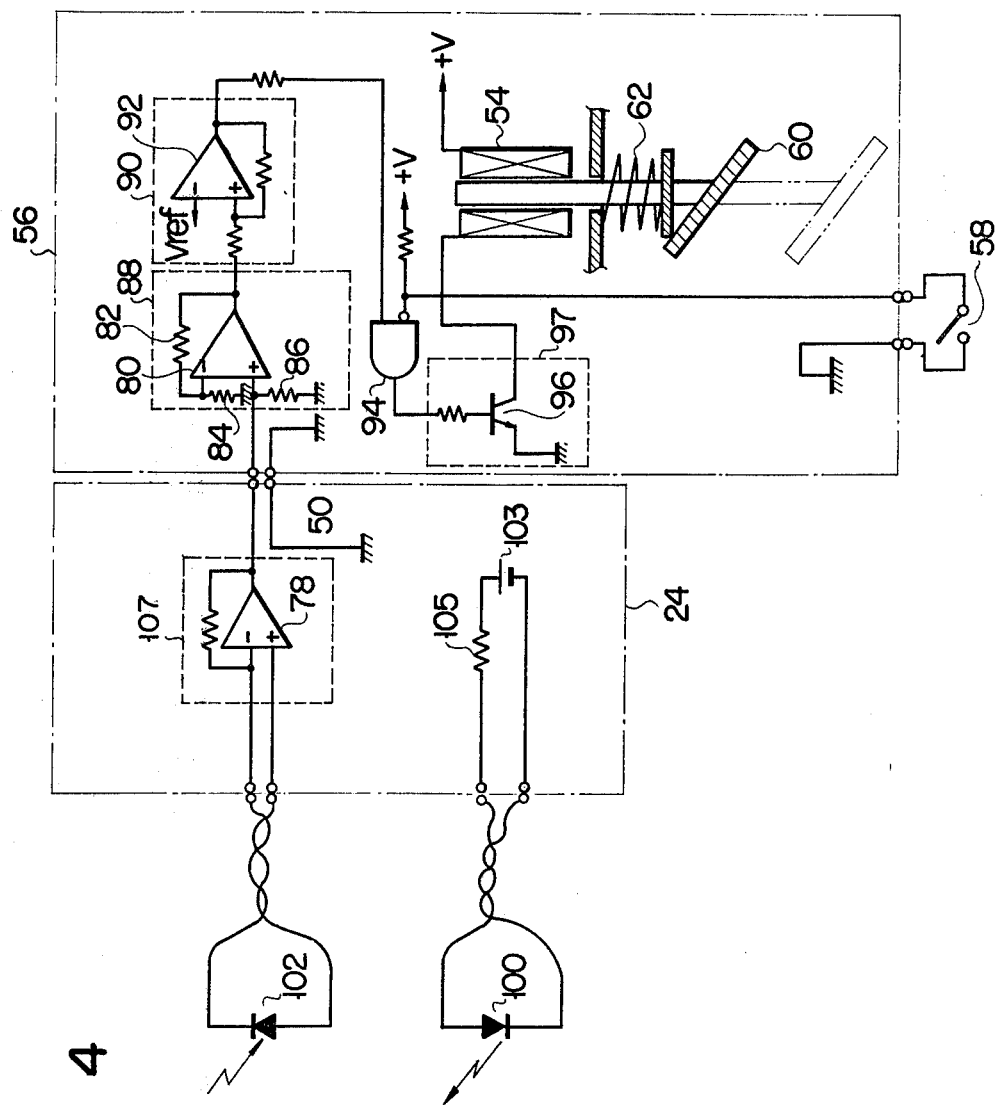
FIG. 4 sets forth the circuit arrangement of the endoscope system of FIG. 3.

With the embodiment of FIG. 4, the approach of the operator 42 to the eyepiece section 6 and his removal therefrom are detected by the intensity of light beams which are issued from the light-emitting element 100, reflected from the operator 42 and caught by the light-receiving element 102. Where the operator 42 approaches a point separated from the eyepiece section 6 at a smaller distance than the prescribed distance, then light beams which are emitted from the light-emitting element 100, reflected from the face of the operator 42 and caught by the light-receiving element 102 reaches a prescribed level of intensity. Therefore, an output current signal from the light-receiving element 102 which carries out for photoelectric conversion of a received light attains a prescribed level. Therefore, an output voltage signal from the current-voltage converter 107 also reaches a prescribed level. At this time the Schmitt circuit 90 of FIG. 4 sends forth a laser beam irradiation-enabling signal to the gate circuit 94, rendering laser beams ready to be emitted. In contrast, when the operator 42 is separated from the eyepiece section 6 at a longer distance than the prescribed distance, then the solenoid control circuit 56 retains a state capable of suppressing the irradiation of laser beams even if the laser beams switch 58 is closed by mistake, thereby reliably preventing the erroneous emission of laser beams.

Figure 5:
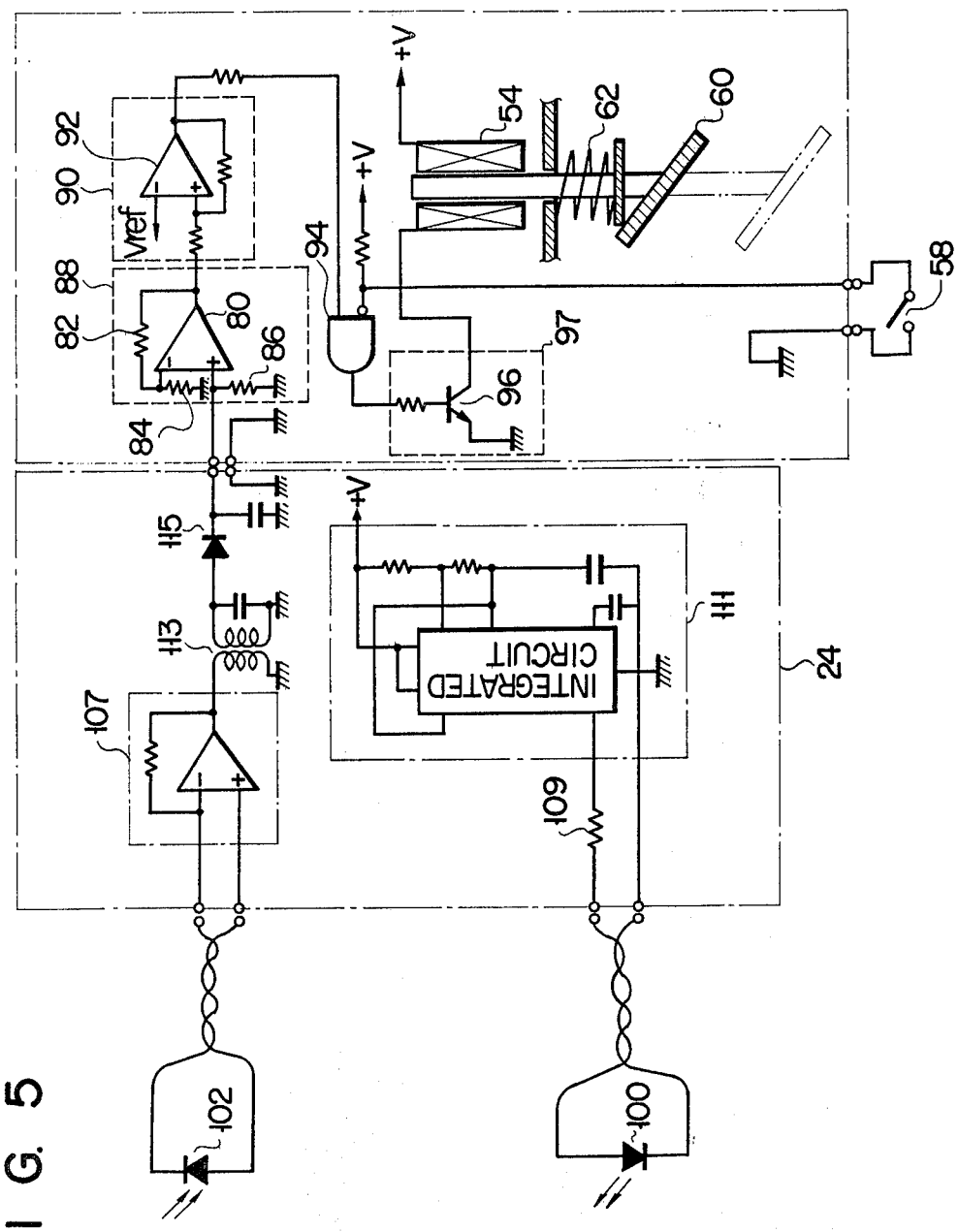
FIG. 5 illustrates the arrangement of a modification of the circuit of FIG. 4.

To prevent the laser knife apparatus 34 from being erroneously rendered ready to emit laser beams due to the projection of a natural or indoor light on the light-receiving element 102, it may be advised previously modulate light beams sent forth from the light-emitting element 100 as shown in FIG. 5, filter a signal denoting a light caught by the light-receiving element 102 and render the laser knife apparatus 34 ready to emit laser beams only upon receipt of a prescribed signal. Namely, to attain the above-mentioned object, the light-emitting element 100 is connected, as shown in FIG. 5, to an integrated circuit, for example, an oscillating circuit 111 consisting of the NE 555 type manufactured by Texas Instruments Co. Inc. through a resistor 109. With the arrangement of FIG. 5, the light-emitting element 100 is actuated at a frequency specified by the oscillating circuit 111. When the operator 42 approaches the eyepiece frame 22 at a prescribed distance, then a light which was sent forth from the light-emitting element 100 and whose intensity was modulated is reflected from the face of the operator 42 and brought into the light-receiving element 102. This light-receiving element 102 receives not only an intensity-modulated light but also a natural or indoor light as a noise. Therefore, the light-receiving element 102 sends forth a mixed current signal, that is, a current signal which has a prescribed frequency and is contaminated by a noise. A band filter 113 and rectifying circuit 115 are connected between a current-voltage converter 107 for converting said mixed current signal into a voltage and an amplifier 88.

The band filter 113 extracts only a voltage signal having a prescribed frequency from the mixed voltage signal delivered from the current-voltage converter 107. The voltage signal having the prescribed frequency is rectified by the rectifying circuit 115. The rectified voltage signal is supplied to the Schmitt circuit 90 through the amplifier 34. As a result, the Schmitt circuit 90 is only supplied with a measurement signal having a level varying with a distance between the eyepiece frame 22 and the face of the operator 42, making it possible to judge whether said distance falls within a prescribed range. With the foregoing embodiment, a light sent forth from the light-emitting element 100 may be weak, because the operator 42 would be prevented from being dazzled by an intense light which might otherwise be issued from said light-emitting element 100. It is preferable for preventing the operator 42 from being dazzled to use an infrared emitting diode as the light emitting element.

The foregoing description refers to the case where a safety device according to a second embodiment of this invention was applied to an endoscope apparatus. Obviously, this invention is also applicable to an optical instrument capable of effecting medical treatment while observation is continued, for example, an operation microscope and rigid endoscope.

Figure 6:
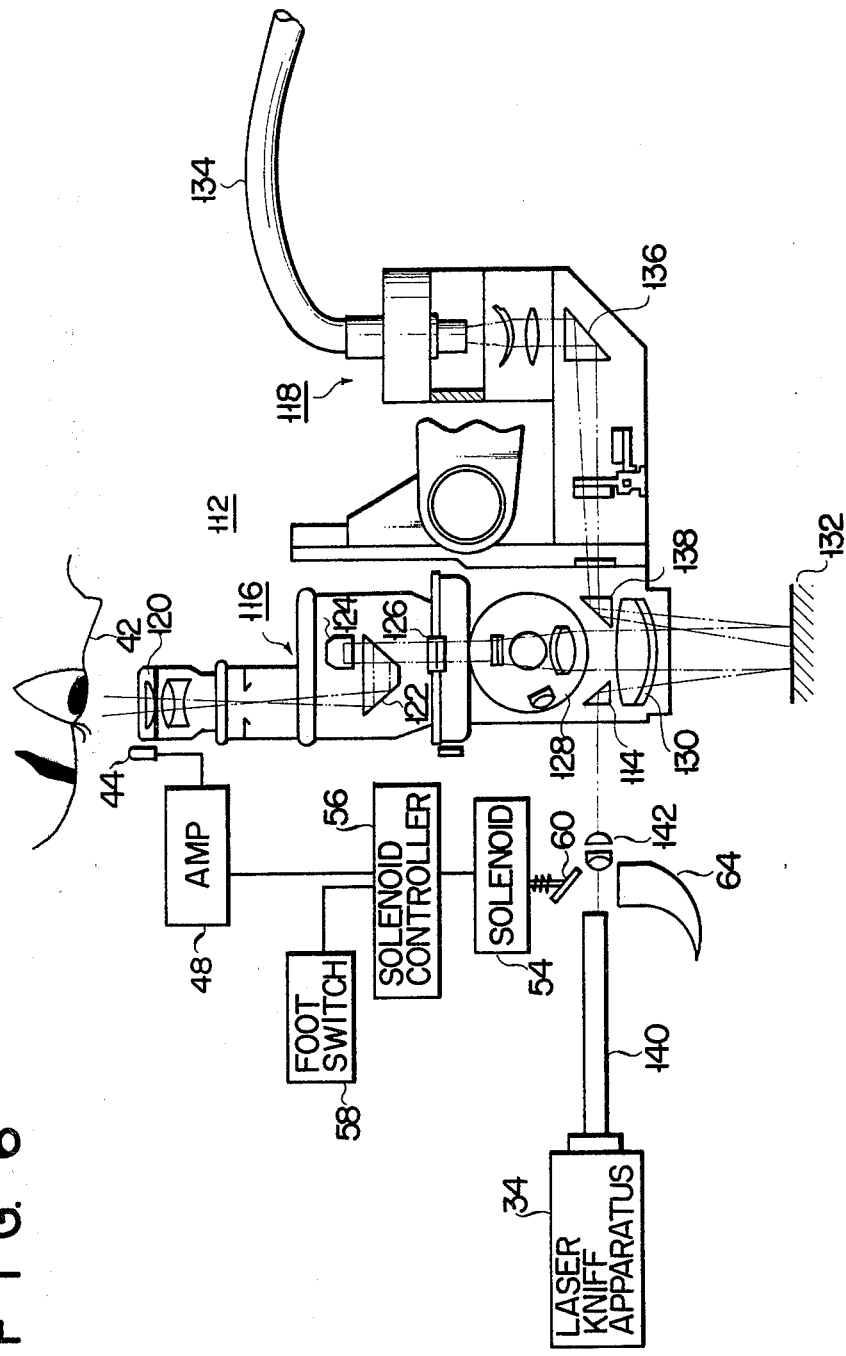
FIG. 6 is a schematic block diagram of an operation microscope system according to a third embodiment of the invention which is provided with a laser knife apparatus.

For instance, it is possible to apply a safety device according to a third embodiment of this invention to a microscope assembly 112 of FIG. 6. As is well known, the microscope assembly comprises a head assembly 116 and illumination light-directing system 118. The head assembly 116 comprises an eyepiece 120, prism 122, mirror 124, lens 126, exchangeable lens assembly 128, and objective lens 130. A patient's coeliac region 132 requiring medical treatment can also be observed by means of the above-mentioned microscope optical system. The illumination light-directing system 118 is connected to one end of a light guide 134 optically coupled to a light source (not shown). An illumination light conducted through the light guide 134 is projected on a coeliac region 132 requiring medical treatment by means of the illumination light-directing system 118 formed of a lens-prism system 136 and prism 138, as well as by means of the object lens 130. The coeliac medical treatment region can be observed in enlargement with the aid of the illumination light. The microscope assembly 112 of FIG. 6 is provided with the laser knife apparatus 34. Optically connected to said laser knife apparatus 34 is a laser beam guide 140 which is formed of a lens, and mirror or fiber bundle to conduct laser beams issued from the laser knife apparatus 34. Provided in the path of laser beams emitted through said laser beam guide 140 are a focusing lens 142 and prism 144 to medically treat a prescribed affected coeliac region 132 by concentrating laser beams thereon. As in the preceding embodiments, a safety device according to the third embodiment of this invention, comprises a mirror 60 which is set in the path of laser beams and can be removed therefrom by the action of the solenoid 54, and an attenuator 64 for attenuating laser beams reflected from the mirror 60. The safety device of the third embodiment of the invention also comprises an infrared ray detector 44 disposed near the eyepiece 120, buffer amplifier 24 and solenoid controller 56. These elements 44, 48, 56 jointly act to prevent the occurrence of the possibility that the solenoid 54 is unnecessarily actuated by the erroneous treading of the foot switch, thereby removing the mirror 60 from the path of laser beams and undesirably projecting laser beams on a normal coeliac tissue around the affected region actually requiring medical treatment.

With an operation microscope equipped with a safety device of FIG. 6 according to the third embodiment of this invention, the solenoid controller 56 maintains the solenoid 54 in a deenergized state, unless the operator 42 looks into the eyepiece 120. Even if the foot switch 58 is depressed by mistake, laser beams issued from the laser knife apparatus 34 are prevented from being unnecessarily concentrated on a normal coeliac tissue around the affected region 132 actually requiring medical treatment. When the operator 42 approaches the eyepiece 120 at a prescribed distance, then the solenoid controller 56 renders the solenoid ready to be energized, thereby bringing laser beams to a state ready to be projected on the affected coeliac region 132 actually requiring medical treatment. Consequently, the operator 42 can emit laser beams on the specified spot of the affected coeliac region 132.

Figure 7:
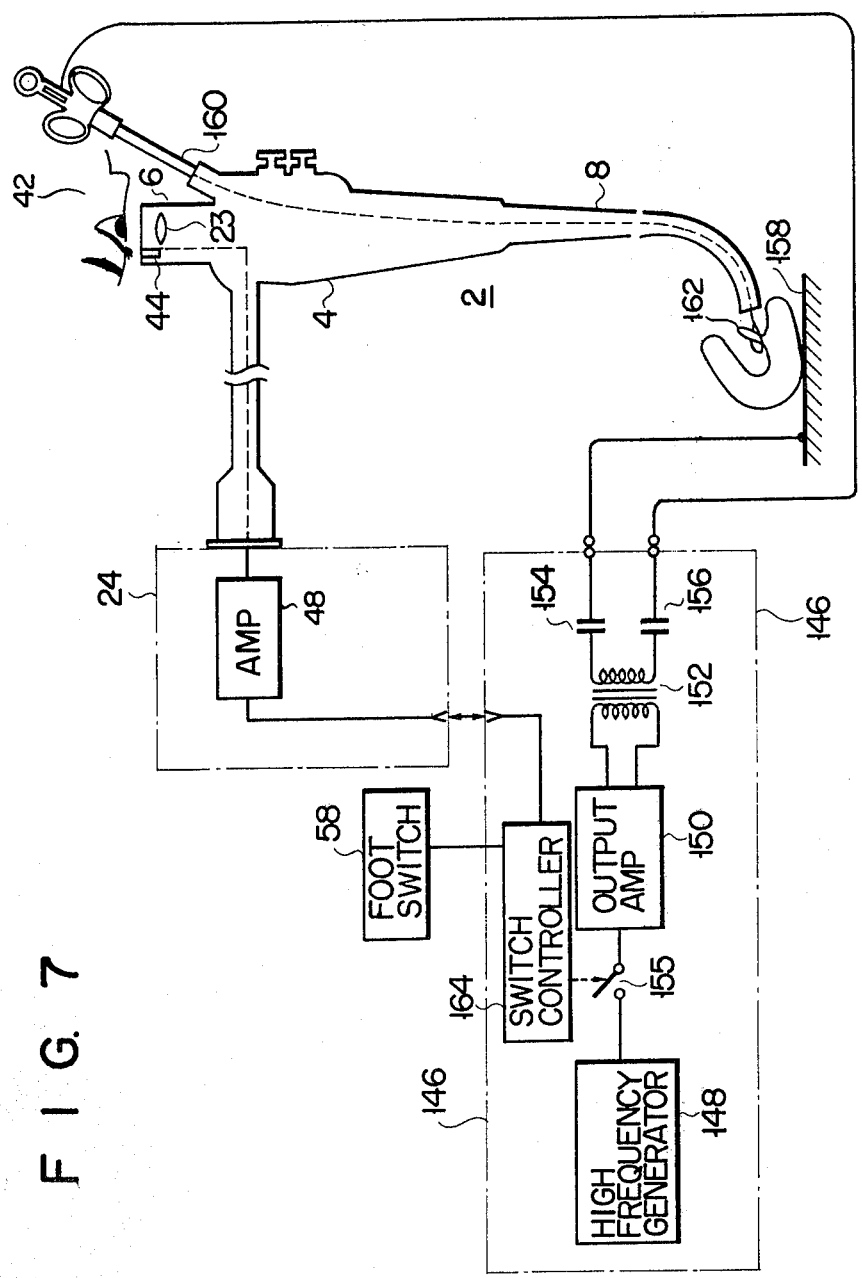
FIG. 7 is a block diagram of an endoscope system according to a fourth embodiment of the invention which is provided with a high frequency electric knife.

The medical treatment system is not limited to the laser knife apparatus 34 of FIG. 6, but may be formed of a high frequency electric knife apparatus 146 of FIG. 7. This high frequency electric knife apparatus 146 comprises a high frequency generator 148 for producing high frequency voltage. Where the foot switch 58 is depressed, and a relay contact 155 is closed then the high frequency current is amplified by an output amplifier 150 and conducted through a passage extending between an electrode 158 fitted to a patient and high frequency probe 160 through a transformer 152 and capacitors 154, 156. The high frequency probe 160 extends through the channel of the endoscope 2 up to the affected coeliac region 162. Therefore, said affected coeliac region 162 is excised and solidified. As in the preceding embodiments, the high frequency electric knife apparatus according to the fourth embodiment of FIG. 7, comprises a safety device formed of a switch controller 164, infrared ray detector 44, and buffer amplifier 48 in order to prevent high frequency current from being concentrated on a normal coeliac tissue around the affected region by the erroneous treading of the foot switch 58. The embodiment of FIG. 7 has substantially the same circuit arrangement as that of FIG. 2, except that the infrared ray detector 44 is fitted to the eyepiece 6 of the endoscope 2; and a switch controller 164 is formed of a relay (not shown) instead of the solenoid 54, said relay being connected to the collector of the transistor 96 of FIG. 2. When the operator 42 approaches the eyepiece 6 at a smaller distance than prescribed, the relay of the switch controller 164 is rendered ready to be energized. When the foot switch 58 is depressed during this period, the relay is energized to close a relay contact 155, allowing high frequency current to be supplied to the effected coeliac region 162. When the operator 42 does not approach the eyepiece 6, the relay remains deenergized, causing the relay contact 155 to be left open.

As described above, this invention renders a medical treatment system ready to be actuated only when observation is carried out. Even if a starting signal is supplied to a medical treatment system by mistake while observation is not carried out, then said medical treatment system is not actuated, thereby suppressing the occurrence of a danger resulting from erroneous operation of said system.

What is claimed is:

1. A medical treatment system having a safety device, the medical treatment system comprising:

a medical optical apparatus having an eyepiece for observing an affected coeliac region of a patient requiring medical treatment;

medical treatment means for medically treating a specified spot of the affected coeliac region;

switch means coupled to said medical treatment means and being operable for selectively energizing said medical treatment means;

detection means for detecting the approach of an operator to said eyepiece, and for generating an output signal which is a function of a distance between the face of the operator and said eyepiece;

judgment means coupled to said detection means and responsive to the output signal of said detection means for judging when the operator is at or closer than a prescribed distance from said eyepiece and for generating a medical treatment-enabling signal when said operator is judged to be at or closer than said prescribed distance from said eyepiece; and medical treatment-disabling means including means for normally maintaining said medical treatment means in a disabled state and for enabling energization of said medical treatment means by operation of said switch means only upon receipt of a medical treatment-enabling signal from said judgment means, whereby said medical treatment means cannot be energized by said switch means when said medical treatment-enabling signal is not generated.

2. The medical treatment system according to claim 1, wherein said medical optical apparatus comprises an endoscope.

3. The medical treatment system according to claim 1, wherein said medical optical apparatus comprises an operation microscope.

4. The medical treatment system according to claim 1, wherein said medical treatment means comprises a laser knife apparatus for projecting laser beams on the specified spot of an affected coeliac region requiring medical treatment thereby to effect the medical treatment.

5. The medical treatment system according to claim 1, wherein said medical treatment means comprises a high frequency electric knife apparatus for supplying high frequency current to the specified spot of an affected coeliac region requiring medical treatment thereby to carry out the medical treatment.

6. The medical treatment system according to claim 1, wherein:

said medical treatment means comprises a laser knife apparatus for projecting laser beams on the specified spot of an affected coeliac region requiring medical treatment thereby to effect the medical treatment; and said medical treatment-disabling means comprises a mirror arranged in a path of laser beams sent forth from said laser knife apparatus, an attenuator for attenuating laser beams reflected from said mirror, and a solenoid coupled to said mirror and which is energized by a medical treatment-enabling signal to remove said mirror from the path of the laser beams to thereby enable the laser beams to be projected on the specified spot of an affected coeliac region.

7. The medical treatment system according to claim 1, wherein:

said medical treatment means comprises a high frequency electric knife apparatus for supplying high frequency current to the specified spot of an affected coeliac region requiring medical treatment thereby to carry out the medical treatment; and said means for maintaining said medical treatment means is a disabled state comprises a normally open contact provided in said high frequency electric knife apparatus and means for closing the normally open contact in response to the medical treatment-enabling signal, thereby allowing for the impression of high frequency voltage on the affected coeliac region from the high frequency electric knife apparatus.

8. The medical treatment system according to claim 1, wherein said detection means comprises an infrared ray detector for detecting infrared rays reflected from the operator.

9. The medical treatment system according to claim 1, wherein said detection means includes a light-emitting element for sending forth a light toward the operator; and a light-receiving element for detecting a light reflected from the operator.

10. The medical treatment system according to claim 9, wherein said detection means comprises an oscillation circuit for supplying current modulated at a specified frequency to said light-emitting element and causing said light-emitting element to send forth a light whose intensity has been modulated; and a filter circuit for extracting only a component having a specified frequency from a light signal detected by the light-receiving element.

11. The medical treatment system according to claim 1, wherein said detection means is provided in said eyepiece.

* * * * *